(12) United States Patent
Alsufyani

(10) Patent No.: US 11,490,925 B1
(45) Date of Patent: Nov. 8, 2022

(54) COMBINATION ULTRASOUND TRANSDUCER AND FAT INJECTING CANNULA

(71) Applicant: Mohammed A. Alsufyani, Riyadh (SA)

(72) Inventor: Mohammed A. Alsufyani, Riyadh (SA)

( * ) Notice: Subject to any disclaimer, the term of this patent is extended or adjusted under 35 U.S.C. 154(b) by 0 days.

(21) Appl. No.: 17/343,141

(22) Filed: Jun. 9, 2021

(51) Int. Cl.
| | |
|---|---|
| *A61B 5/0538* | (2021.01) |
| *A61B 5/0537* | (2021.01) |
| *A61B 5/00* | (2006.01) |
| *A61B 17/34* | (2006.01) |
| *A61B 8/08* | (2006.01) |

(52) U.S. Cl.
CPC ...... *A61B 17/3403* (2013.01); *A61B 17/3421* (2013.01); *A61B 8/0841* (2013.01); *A61B 17/3423* (2013.01); *A61B 2017/3413* (2013.01)

(58) Field of Classification Search
CPC .... A61B 2017/32007; A61B 17/22012; A61B 17/320068; A61B 10/0233; A61B 2010/0208; A61B 5/0538; A61B 5/0537; A61B 5/6848; A61B 5/4872; A61N 2005/1011; A61M 2202/08
See application file for complete search history.

(56) References Cited

U.S. PATENT DOCUMENTS

| | | | |
|---|---|---|---|
| 5,437,283 A | 8/1995 | Ranalletta | |
| 8,882,792 B2 | 11/2014 | Dietz | |
| 10,004,844 B2 | 6/2018 | Cheng | |
| 10,751,246 B2 | 8/2020 | Kaila | |
| 10,828,059 B2 | 11/2020 | Price | |
| 2002/0148277 A1* | 10/2002 | Umeda | A61B 8/12 73/1.82 |
| 2009/0171266 A1 | 7/2009 | Harris | |
| 2010/0036245 A1* | 2/2010 | Yu | A61N 5/1027 600/439 |
| 2011/0166451 A1* | 7/2011 | Blaivas | A61B 8/461 600/439 |
| 2011/0313345 A1* | 12/2011 | Schafer | A61B 17/22012 604/22 |
| 2012/0265072 A1* | 10/2012 | Matlock | A61K 35/35 424/574 |
| 2012/0277698 A1* | 11/2012 | Andrew | A61B 17/3203 604/319 |
| 2013/0131635 A1* | 5/2013 | Rimsa | A61L 27/3604 604/152 |
| 2013/0150825 A1* | 6/2013 | Rimsa | A61M 5/2053 604/152 |
| 2013/0261606 A1* | 10/2013 | Andrew | A61B 17/320016 604/542 |
| 2013/0310748 A1* | 11/2013 | Cheng | A61M 5/142 604/151 |
| 2015/0032143 A1* | 1/2015 | Khouri | A61B 17/3417 606/186 |

(Continued)

*Primary Examiner* — Baisakhi Roy
(74) *Attorney, Agent, or Firm* — Neustel Law Offices

(57) ABSTRACT

A medical device for injecting fat while simultaneously allowing the injection site to be viewed with ultrasound. The device may comprise a handle with a front portion and a rear portion, a cannula having a cannula tip, extending from the front portion of the handle, and an ultrasound probe attached to the handle, the ultrasound probe comprising an ultrasound head. The ultrasound head is aligned with and spaced apart from the cannula tip, and remains so aligned during the injection process so that the injection area may be continuously viewed during the procedure.

18 Claims, 3 Drawing Sheets

(56) References Cited

U.S. PATENT DOCUMENTS

| | | | |
|---|---|---|---|
| 2015/0080710 A1* | 3/2015 | Henkel | A61B 8/0833 |
| | | | 600/424 |
| 2016/0361476 A1* | 12/2016 | Huang | C12M 45/02 |
| 2017/0274011 A1 | 9/2017 | Garibyan | |
| 2019/0083234 A1* | 3/2019 | Sforza | A61M 5/3286 |
| 2019/0105433 A1* | 4/2019 | Hagarty | A61M 1/0062 |
| 2020/0305927 A1* | 10/2020 | Grim | A61B 8/4494 |
| 2021/0093757 A1* | 4/2021 | Turer | A61M 1/73 |
| 2021/0219947 A1* | 7/2021 | Azzara | A61B 8/4488 |
| 2022/0079874 A1* | 3/2022 | Garibyan | A61K 47/10 |

\* cited by examiner

COMBINATION ULTRASOUND TRANSDUCER AND FAT INJECTING CANNULA

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND

The described example embodiments in general relate to cannulas and ultrasound probes for use with autologous fat transplantation.

Autologous fat transplantation, or fat grafting, transfers fat from areas of the body where there may be an excess of fat, and injects it into areas that may be either lacking in volume, or where a person desires more fat or an improved shape, such as the buttocks, breasts, hands, or face. Autologous fat injection can result in a more permanent change than that provided by other methods, such as the use of temporary fillers. In other words, fat transfer results can be long-lived, safe, and natural. When used for a fuller buttock, liposuction can be used not only to sculpt the area surrounding the injection location, but may also be used to collect the autologous fat that will be injected.

SUMMARY

Some of the various embodiments of the present disclosure relate to a combination ultrasound transducer and fat injecting cannula that can allow a user to inject fat into a patient while viewing tissue in the injection area with a probe, all while using the device with one hand. Some of the various embodiments of the present disclosure include a handle comprising a front portion and a rear portion. A cannula having a cannula tip generally extends from the front portion of the handle, and further, an ultrasound probe is also attached to the handle, the ultrasound probe comprising an ultrasound head. The ultrasound head is aligned with and spaced apart from the cannula tip, such that a user can view tissue in close proximity to the cannula tip. In some other embodiments, the ultrasound probe is attached so that it can be pivoted to change the spacing between the ultrasound head and the cannula tip so that the apparatus can be used to inject fat at different depths.

There has thus been outlined, rather broadly, some of the embodiments of the present disclosure in order that the detailed description thereof may be better understood, and in order that the present contribution to the art may be better appreciated. There are additional embodiments of that will be described hereinafter and that will form the subject matter of the claims appended hereto. In this respect, before explaining at least one embodiment in detail, it is to be understood that the various embodiments are not limited in its application to the details of construction or to the arrangements of the components set forth in the following description or illustrated in the drawings. Also, it is to be understood that the phraseology and terminology employed herein are for the purpose of the description and should not be regarded as limiting.

To better understand the nature and advantages of the present disclosure, reference should be made to the following description and the accompanying figures. It is to be understood, however, that each of the figures is provided for the purpose of illustration only and is not intended as a definition of the limits of the scope of the present disclosure. Also, as a general rule, and unless it is evidence to the contrary from the description, where elements in different figures use identical reference numbers, the elements are generally either identical or at least similar in function or purpose.

DETAILED DESCRIPTION

Figure 1:
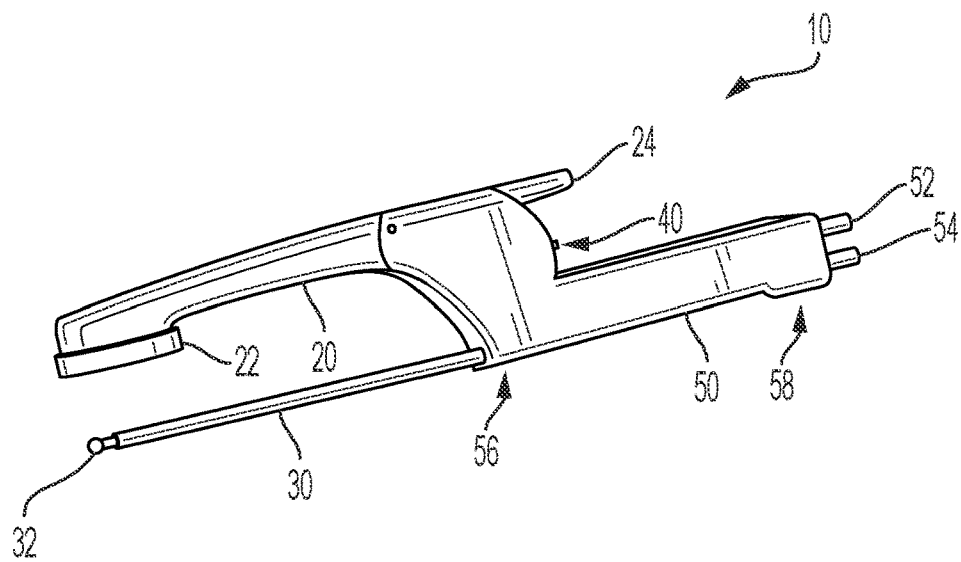
FIG. 1 is a perspective view of a combination ultrasound transducer and fat injecting cannula in accordance with an example embodiment.

A. Overview.

Some of the various embodiments of the present disclosure relate to a medical device 10 that can allow a user to inject fat into a patient while viewing tissue in the injection area with a probe. Unlike other methods, the injection and positioning of the ultrasound probe can be performed while using the device with one hand. Some of the various embodiments of the present disclosure include a handle 50 comprising a front portion 56 and a rear portion 58. A cannula 30 having a cannula tip 32 generally extends from the front portion 56 of the handle 50, and further, an ultrasound probe 20 is also attached to the handle 50, the ultrasound probe 20 comprising an ultrasound head 22.

The ultrasound head 22 is aligned with and spaced apart from the cannula tip 32, such that a user can view tissue in close proximity to the cannula tip 32 while injecting fat or positioning the cannula 30. In some embodiments, the ultrasound probe 20 is attached so that it can be pivoted in or about the handle 50 to change the spacing or spatial relationship between the ultrasound head 22 and the cannula tip 32 so that the medical device 10 can be used to inject fat at different depths in a patient's tissue.

In some embodiments, the medical device 10 can also include a lock 40 usable to hold the ultrasound probe 20 and head 22 in a fixed position relative to the cannula tip 32. For example, if the ultrasound probe 20 is pivotally connected to the handle 50, the lock may be adapted to prevent the ultrasound probe from pivoting, either in a single direction, or in any direction. In some embodiments, the medical device 10 may have a lock that is spring-loaded, such that it is biased in the locked position. In addition, the ultrasound probe 20 can comprise a lever 24 adaptable to adjust the distance between the ultrasound head 22 and the cannula tip 32.

In some embodiments of the medical device, the ultrasound head 22 may be a linear ultrasound head. A linear probe will typically produce a rectangular field of view that corresponds with its linear footprint. A linear probe is also a high frequency probe that provides very good resolution. The linear ultrasound probe can be used in Doppler mode, as well as other modes. In Doppler mode, a user can detect blood flow in vessels, and may thus be able to avoid unwanted positioning of the cannula tip 32 relative to blood vessels.

In use, the medical device 10 may be constructed such that the ultrasound head 22 is aligned with the cannula tip 32 such that a placement of the cannula tip 32 within a patient is within an ultrasound field of the ultrasound head. For example, the ultrasound probe 20 can be pivotally connected to the handle 50 such that the distance between the ultrasound head 22 and the cannula tip 32 is adjustable, and wherein the placement of the cannula tip 32 within a patient remains within the ultrasound field when the ultrasound probe 20 is pivoted to adjust the distance.

In some embodiments, the medical device 10 may further comprise a fat transfer port 54 at the rear portion 58 of the handle 50, wherein the fat transfer port 54 is in fluid communication with the cannula 30. The handle 50 may also comprise a wire connection point 52 for the ultrasound probe 20 near the rear portion 58 of the handle 50.

The medical device 10 may be used by adjusting a position of the ultrasound head 22 relative to the cannula tip 32 to a first position. Next, the cannula may be inserted into a fat injection area 80 of a patient. The method may comprise contacting a patient's skin with the ultrasound head 22 proximate the fat injection area 80, and injecting fat in the fat injection area 80 while viewing a placement of the cannula tip 32 inside the patient on an ultrasound monitor 70.

The method described above may further comprise adjusting the position of the ultrasound head 22 relative to the cannula tip 32 to a second position after adjusting to the first position. In addition, the method may include locking the ultrasound head 22 in the second position relative to the cannula tip 32, by operating the lock 40. The placement of the cannula tip 32 can be viewed on the ultrasound monitor 70 in Doppler mode, to show the presence of blood vessels (because the flow of blood can be seen or interpreted in Doppler mode). Once the cannula 30 is properly positioned, as determined by viewing the ultrasound from ultrasound head 22, fat may be injected into the injection area 80 through pump 60, which is connected to fat transfer port 54 near the rear portion 58 of handle 50. As mentioned previously, the fat transfer port 54 is in fluid communication with the cannula 30, such that when pump 60 is activated, fat is injected at the cannula tip 32.

B. Handle.

Some example embodiments of the medical device 10 include a handle 50, which is ergonomically designed and allows for adjustment as well. As best shown in FIGS. 1-4 and 7-9, the handle 50 is comprised of a rear portion 58 and a front portion 56. A user, such as a surgeon or doctor, can hold the handle 50 in one hand and position a fat-injection cannula 30 and an ultrasound probe 20 and ultrasound head 22 at the same time. Near or at the rear portion 58 of the handle 50, there may be a fat transfer port 54, which is in fluid communication with the cannula 30, such that fat pumped into or introduced into the fat transfer port 54 can be injected into a patient at a desired location. As shown in FIGS. 1-4 and 6-9, the handle 50 may also include a wire connection point 52 near fat transfer port 54, at the rear portion of handle 50. The wire connection point 52 is usable to electrically connect the ultrasound probe 20 to an ultrasound monitor 70, and any other components, as necessary.

In addition to discrete ports and connection points at the rear portion 58 of the handle, the medical device 10 may also include other configurations. For example, instead of fat transfer port 54, the device 10 may include a tube that enters the handle 50 directly, and has a suitable length such that it can be directly connected to pump 60. Similarly, the medical device 10 may not necessarily include a wire connection point 52 (which may be a connector, for example), but may similarly have a longer wire or cable that extends out of the handle 50 (near the rear portion 58) and connects directly at its far end to an ultrasound monitor 70 or other ultrasound equipment.

Figure 3:
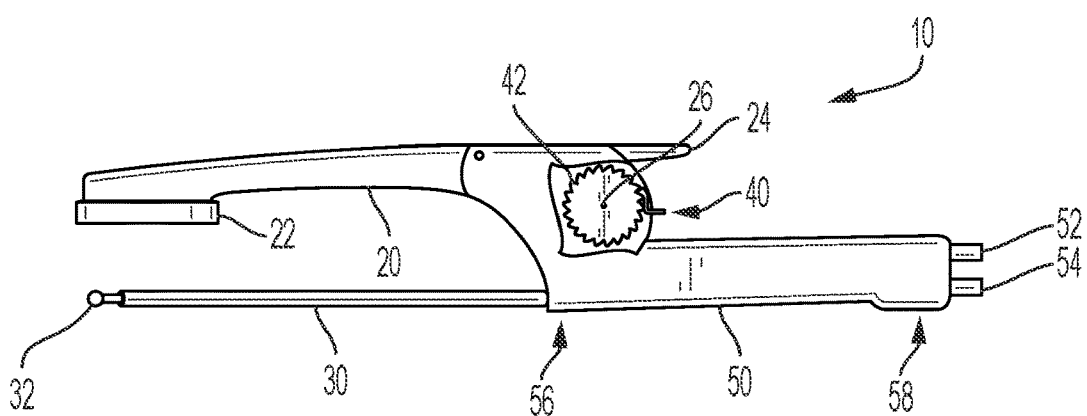
FIG. 3 is a side view of a combination ultrasound transducer and fat injecting cannula in accordance with an example embodiment.

Within the handle 50, some embodiments may include a lock 40. The lock 40 operates to lock the ultrasound probe 20 in position. As shown by comparing FIGS. 3 and 4, as well as 8 and 9, the ultrasound probe 20 may be pivoted within or relative to handle 50. Accordingly, the ultrasound probe 20 may be pivotally connected to the handle 50 to pivot about point 26 (although the probe may pivot about another point of the handle as well), as shown in FIGS. 3 and 5. FIGS. 3 and 5 include cutaway views to show some lock components within the handle. As shown in FIG. 5, the device 10 includes a lock wheel 42 that will move when the ultrasound probe 20 is pivoted. Thus, if lock wheel 42 is prevented from rotating, in either one or two directions, the ultrasound probe 20 will also be locked in position. As mentioned, the lock 40 can be bidirectional or unidirectional. The ultrasound probe 20 may be linked or connected to lock wheel 42 inside the handle 50 by a probe connecting member 28, such that when the ultrasound probe 20 is pivoted, the lock wheel 42 rotates.

At the front portion of the handle 50, the cannula 30 extends forward, away from the fat transfer port 54 and wire connection point 52. The cannula 30 ends at a tip 32, which may be any number of shapes or sizes. The tip 32 is the injection end of the cannula 30, where fat emerges when forced through the cannula 30. The handle 50 allows for good control of the position of the cannula 30 and its tip 32. The handle also serves to hold or maintain the ultrasound probe 20 and ultrasound head 22 in a fixed position relative to the cannula tip 32. As will be discussed in more detail below, this allows a surgeon to manipulate the probe and the cannula with just one hand, while allowing the use of the other hand to control and palpate the injection area.

C. Lock.

Within the handle 50, some embodiments may include a lock 40. The lock 40 operates to lock the ultrasound probe 20 in position. As shown by comparing FIGS. 3 and 4, as well as FIGS. 8 and 9, the ultrasound probe 20 may be pivoted within or relative to handle 50. Accordingly, the ultrasound probe 20 may be pivotally connected to the handle 50 to pivot about point 26 (although the probe may pivot about another point of the handle as well), as shown in FIGS. 3 and 5. FIGS. 3 and 5 include cutaway views to show some lock components within the handle. As shown in FIG. 5, the device 10 includes a lock wheel 42 that will move when the ultrasound probe 20 is pivoted. Thus, if lock wheel 42 is prevented from rotating, in either one or two directions, the ultrasound probe 20 will also be locked in position. As mentioned, the lock 40 can be bidirectional or unidirectional. The lock mechanism may include a lock recess 44 that engages a lock tooth 46 to prevent rotation of the lock wheel 42, and accordingly, the ultrasound probe 20 and head 22. Locking the ultrasound probe 20 in this manner ensures that a user is able to maintain pressure and good contact between the ultrasound head 22 and the patient's skin, resulting in a good ultrasound view of the cannula 30, the cannula tip 32, and the fat injection area 80.

The lock 40 may be held in a desired position (e.g., locked or unlocked) by friction between the lock 40 and the channel 47, by spring pressure, or a combination of the two. In addition, the lock 40 may be configured to move in a linear fashion, or it may pivot about lock pivot 43, as shown, for example, in FIG. 5. In addition, a spring 48 can be connected as shown, above lock pivot 43 (which can be a fixed, internal portion of handle 50), so that the spring 48 urges the lock 40 into the "engaged" position. One end of the spring 48 may be connected to the lock at connection 49, as shown. The opposite, fixed end of spring 48 may be secured to a portion of the handle 50 at a spring anchor point 45.

As shown, for example, in FIGS. 1-4, the lock 40 may be located where the handle 50 rises toward the adjustment lever 24, so that both the lock 40 and the adjustment lever 24 can be operated with a user's thumb, while holding and manipulating handle 50. This provides not only convenience, but safety, because it allows operation of the device 10 without taking the user's eyes off of other areas, such as the patient's injection site, or the ultrasound monitor 70.

D. Ultrasound Probe and Head.

As mentioned briefly above, the ultrasound head 22 is aligned with and spaced apart from the cannula tip 32, such that a user can view tissue in close proximity to the cannula tip 32 while injecting fat or positioning the cannula 30. This is shown, for example, in FIGS. 1-4, and is perhaps best shown in use on a patient in FIGS. 8-9. The ultrasound probe 20 is attached to the handle 50 so that it can be pivoted in or about the handle 50 to change the spacing or spatial relationship between the ultrasound head 22 and the cannula tip 32 so that the medical device 10 can be used to inject fat at different depths in a patient's tissue.

The ultrasound head 22 may be a linear ultrasound head. A linear probe will typically produce a rectangular field of view that corresponds with its linear footprint. A linear probe is also typically a high frequency probe that provides very good resolution. The linear ultrasound probe can be used in Doppler mode, as well as other modes. In Doppler mode, a user can detect blood flow in vessels, and may thus be able to avoid unwanted positioning of the cannula tip 32 relative to blood vessels.

In use, the medical device 10 may be constructed such that the ultrasound head 22 is aligned with the cannula tip 32 such that a placement of the cannula tip 32 within a patient is within an ultrasound field of the ultrasound head. For example, the ultrasound probe 20 can be pivotally connected to the handle 50 such that the distance between the ultrasound head 22 and the cannula tip 32 is adjustable, and wherein the placement of the cannula tip 32 within a patient remains within the ultrasound field when the ultrasound probe 20 is pivoted to adjust the distance. This relationship may be achieved by having the cannula tip 32 placed more "forward" (i.e., toward the left in FIG. 8) when the ultrasound head 22 is in a closed position, wherein the head 22 is as close to tip 32 as it can be. Accordingly, when the device 10 is opened further, by pivoting the ultrasound head 22 farther away from the cannula tip 32, the tip is still well within the ultrasound field of view. This relationship can be seen to hold even in the more extreme opening shown in FIG. 4.

Figure 2:
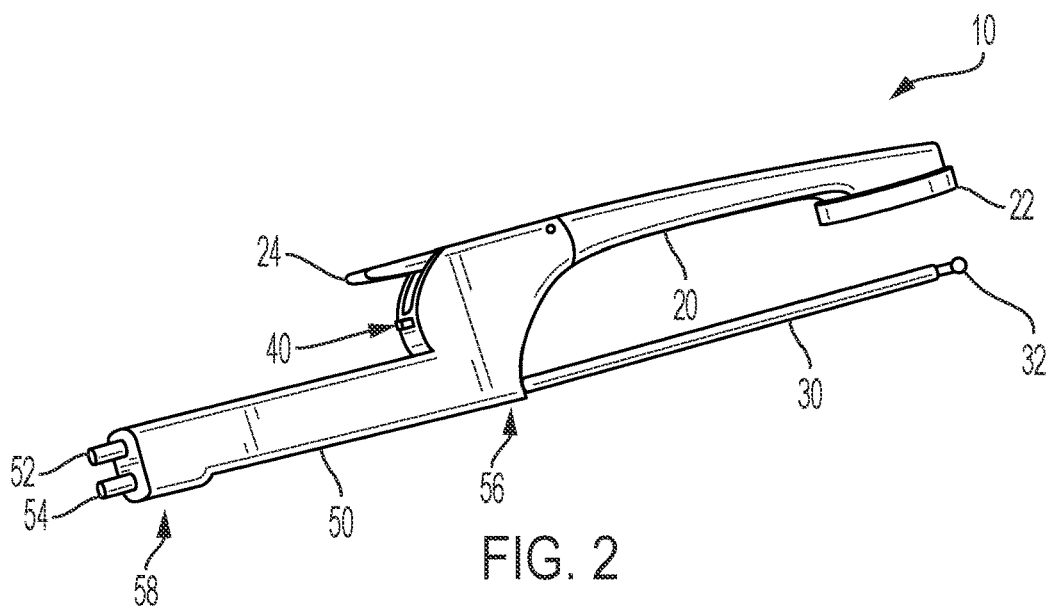
FIG. 2 is another perspective view of a combination ultrasound transducer and fat injecting cannula in accordance with an example embodiment.
Figure 4:
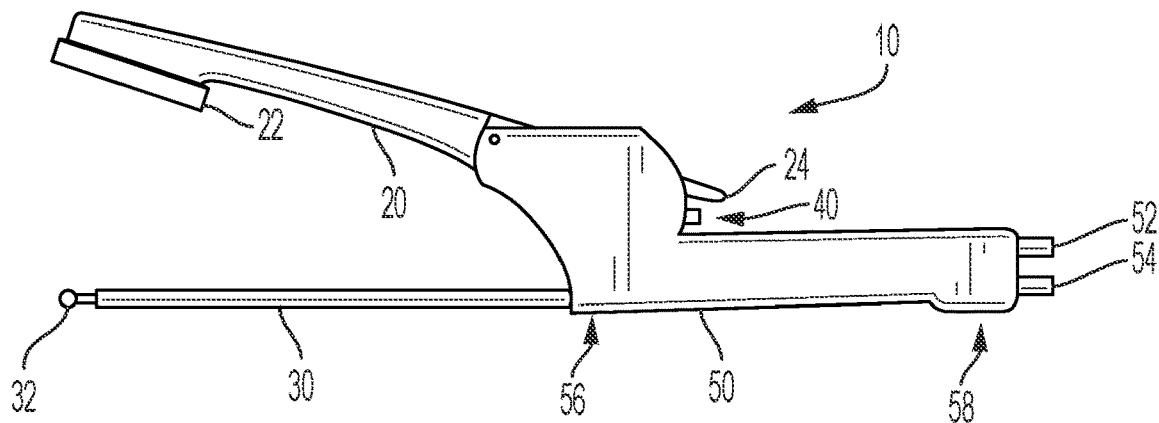
FIG. 4 is another side view of a combination ultrasound transducer and fat injecting cannula in accordance with an example embodiment.
Figure 5:
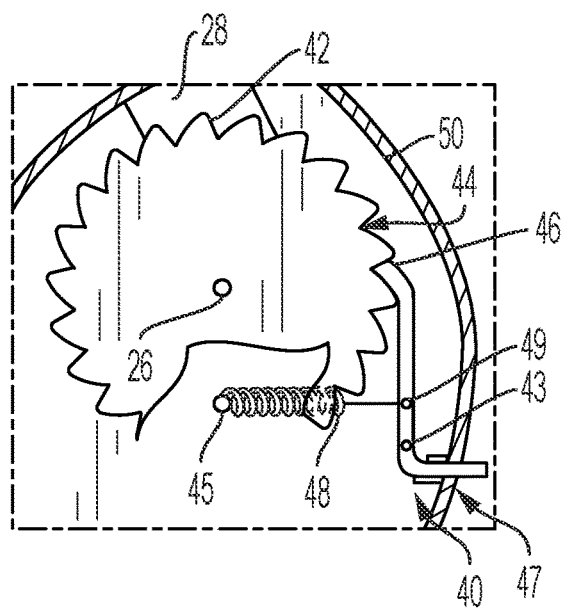
FIG. 5 is a detail view of a lock mechanism usable with a combination ultrasound transducer and fat injecting cannula in accordance with an example embodiment.
Figure 6:
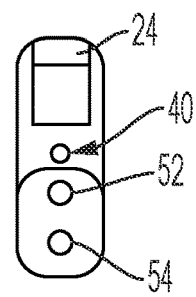
FIG. 6 is a rear view of a combination ultrasound transducer and fat injecting cannula in accordance with an example embodiment.

The ultrasound probe 20 can be adjusted relative to the handle 50 with the use of adjustment lever 24, which, as best shown in FIGS. 2 and 4, extends just beyond the handle 50 near, but above, the front portion 56 of the handle 50. This placement allows for easy, ergonomic operation of the lever 24 to adjust the spacing or position of the ultrasound head with a user's thumb. In most instances, the medical device 10 will be held in the user's dominant hand.

E. Operation of Preferred Embodiment.

For autologous fat transfer, fat is typically harvested from one part of the body, purified and washed, and then reinjected into areas where augmentation is desired. It may be necessary to repeat this procedure more than once to achieve the desired effect. The site selected for fat removal may be treated with a local anesthetic, after which a small incision can be made in the area for harvesting fat. The cannula 30 may be used for the fat removal as well as the fat injection.

Figure 7:
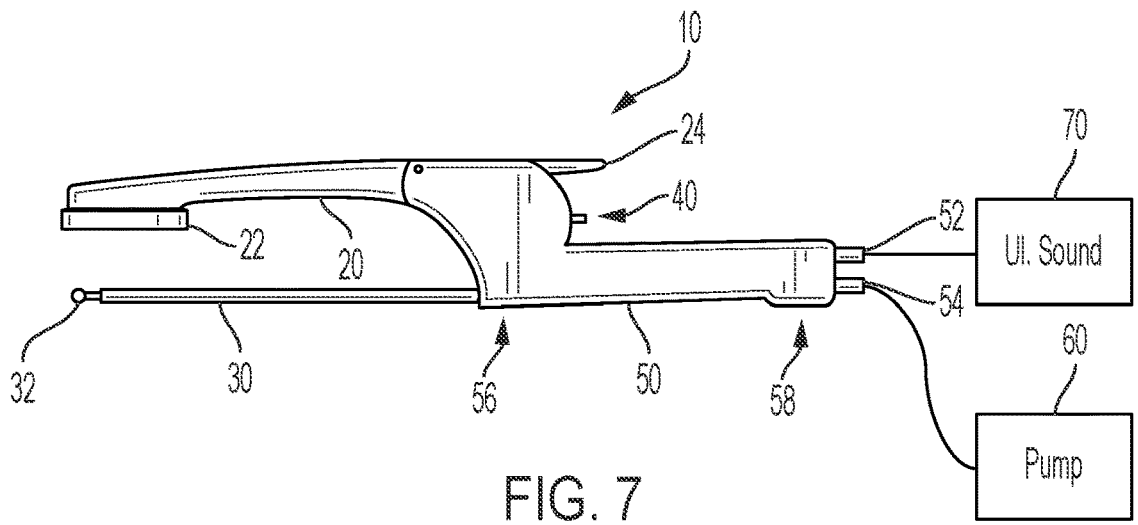
FIG. 7 is a side view of a combination ultrasound transducer and fat injecting cannula connected in a system in accordance with an example embodiment.
Figure 8:
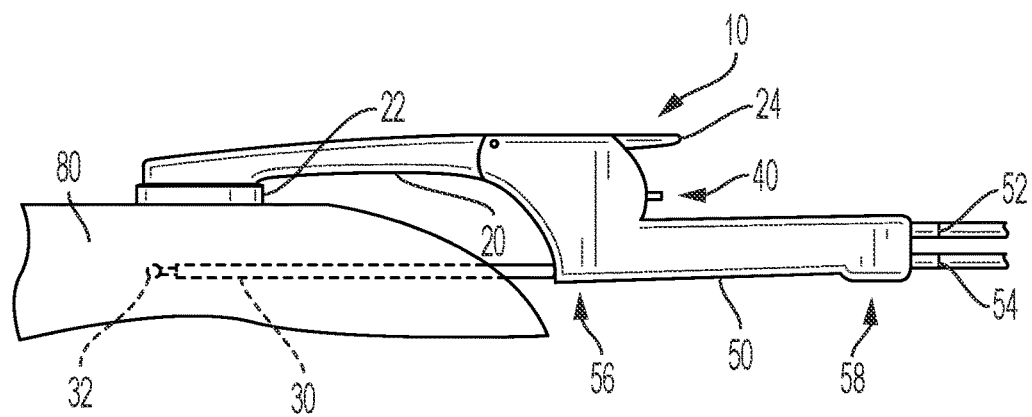
FIG. 8 is a side view of a combination ultrasound transducer and fat injecting cannula in use in accordance with an example embodiment.
Figure 9:
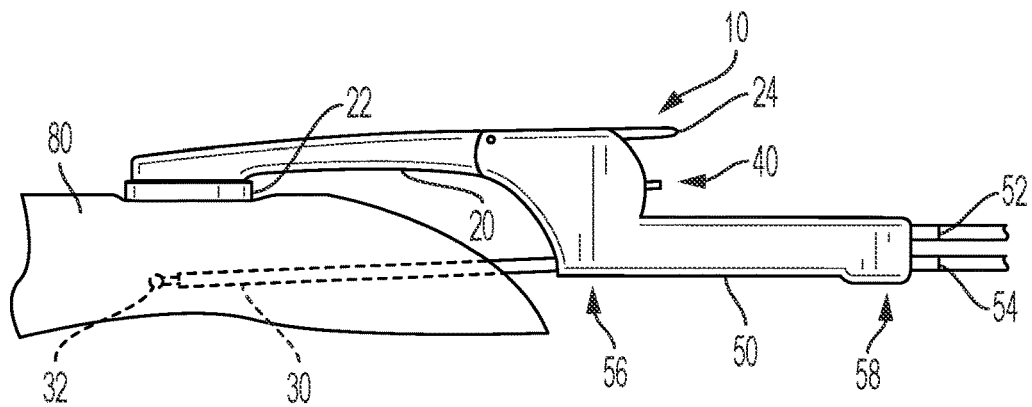
FIG. 9 is another side view of a combination ultrasound transducer and fat injecting cannula in use in accordance with an example embodiment.

Next, the area to receive the fat injection is prepared, similar to that described above, including a sterile incision. The cannula 30 is inserted into the incision, after the surgeon has adjusted the distance (i.e., a first distance) between the ultrasound head 22 and the cannula. The surgeon may decide to begin with the ultrasound head 22 adjusted to a wide open position, as shown in FIG. 4, or in a closed position, as shown in FIGS. 7-8. As desired, the ultrasound probe can either be locked or unlocked at the start of the procedure, per the surgeon's preference. After adjusting the position of the ultrasound head 22, the cannula is inserted into the patient's tissue at the injection area 80, as best shown in FIGS. 8 and 9.

The procedure of autologous fat transfer, especially for buttock augmentation, has been associated with increased morbidity and mortality secondary to inadvertent intravascular placement of the injected fat. Even in the hands of experienced surgeons, it is difficult to accurately place the fat with absolute certainty and accuracy, unless the injection site can be visualized. Techniques that utilize ultrasound probes to increase the safety of this procedure have been suggested. Such techniques give the surgeon the advantage of visualization of the structured anatomy of the fat layers and the muscles that lie beneath. Such visualization can be used with Doppler mode, to further assist a surgeon in locating and avoiding major vessels.

Until now, use of ultrasound in autologous fat transfer has been hindered by the fact that the surgeon would have to juggle the ultrasound probe in one hand and the injection cannula with the other, losing the advantage of using the non-dominant hand for palpating the location of the cannula used to inject the fat and the area where the fat is being placed. In addition, the surgeon needs to balance the movement of both the ultrasound probe and the injection cannula simultaneously to visualize the structures and assertion of the injection level as well, which turns out to be quite challenging.

The new design of medical device 10 makes it possible to use one hand, usually the dominant one, to control the movement of both the ultrasound probe 20 and the injection cannula 30, with a real-time visualization of the fat layers, muscles, vessels, and knowledge of the level that the fat is being placed, and allows this to be done continuously. The medical device 10 also helps free the non-dominant hand to control and palpate the area of injection without the surgeon needing to control both instruments with two hands while also palpating the area.

To begin the injection procedure, the medical device 10, and specifically, ultrasound probe 20, is typically connected to an ultrasound monitor 70 or other ultrasound equipment via wire connection point 52, as shown in FIG. 7. The device 10 is also connected to a pump 60, which is fluidly connected to fat transfer port 54. Port 54 is also in fluid communication with cannula 30. Once the device is connected, the ultrasound head 22 is brought into, or maintained in, contact with the patient's skin just above the precise injection site. The ultrasound probe 20 and the fat injecting cannula 30 are held in positional relationship with each other by the ergonomically designed handle 50. The use of the medical device 10 for this procedure increases the safety and precision of placing the injected autologous fat, due to real-time visualization of the injection area 80 through use of the ultrasound probe 20.

As mentioned above and as shown by comparison of FIGS. 8 and 9, the device can be used to view the injection via ultrasound, at different depths. As shown, the cannula tip 32 is at a greater depth in FIG. 9 than it is in FIG. 8. The ultrasound probe 20 can be locked at any depth after initial insertion of the cannula 30, and this process of determining the depth can be aided in real time by viewing the image produced by the ultrasound head 22 on monitor 70. The position of the ultrasound head 22, and probe 20, is adjusted by operation of lever 24, typically with a surgeon's dominant hand and the surgeon is also holding handle 50. The distance between the ultrasound head 22 and the cannula tip 32 can be lock by a surgeon, typically by using the thumb of the dominant hand to operate the lock 40 by either sliding it or pressing it up or down.

The lock mechanism may include a lock recess 44 that engages a lock tooth 46 to prevent rotation of the lock wheel 42, and accordingly, the ultrasound probe 20 and head 22. Locking the ultrasound probe 20 in this manner ensures that a user is able to maintain pressure and good contact between the ultrasound head 22 and the patient's skin, resulting in a good ultrasound view of the cannula 30, the cannula tip 32, and the fat injection area 80. In addition to the embodiment shown, other lock arrangements are possible. For example, the lock 40 may comprise a lock recess 44 of a different shape or profile, such as a square or rectangular notch, with a lock tooth 46 shaped and sized to fit the recess 44 (whatever shape it has). A square or rectangular lock would be usable to lock the ultrasound probe 20 in position so that it would not open wider or narrower—in other words, so it would not be pivotable at all until the lock is released.

Thus, the use of the device 10 may comprise adjusting a position of the ultrasound head 22 relative to the cannula tip 32 to a first position, inserting the cannula 30 into a fat injection area 80 of the patient, contacting the patient's skin with the ultrasound head 22 proximate the fat injection area 80, and injecting fat in the fat injection area 80 while viewing the placement of the cannula tip 32 in real time inside the patient, on an ultrasound monitor 70. The method may further comprise adjusting the position of the ultrasound head 22 relative to the cannula tip 32 to a second position after adjusting it to the first position. This latter method may also include locking the ultrasound head 22 in the second position relative to the cannula tip 32 during fat injection. Of course, the depth of the cannula tip 32 can be changed repeatedly, with the ultrasound head 22 being locked in position following adjustment.

The placement of the cannula tip can advantageously be viewed on the ultrasound monitor 70 in Doppler mode. Using any of various Doppler modes (i.e., color Doppler or power Doppler) can help the surgeon visualize blood flow, and thus, the presence and location of blood vessels relative to the cannula tip 32, and thus allow such vessels to be avoided.

Unless otherwise defined, all technical and scientific terms used herein have the same meaning as commonly understood by one of ordinary skill in the art to which this invention belongs. Although methods and materials similar to or equivalent to those described herein can be used in the practice or testing of the various embodiments of the present disclosure, suitable methods and materials are described above. All patent applications, patents, and printed publications cited herein are incorporated herein by reference in their entireties, except for any definitions, subject matter disclaimers or disavowals, and except to the extent that the incorporated material is inconsistent with the express disclosure herein, in which case the language in this disclosure controls. The various embodiments of the present disclosure may be embodied in other specific forms without departing from the spirit or essential attributes thereof, and it is therefore desired that the various embodiments in the present disclosure be considered in all respects as illustrative and not restrictive. Any headings utilized within the description are for convenience only and have no legal or limiting effect.

What is claimed is:

1. A medical device, comprising:
a fat-injecting cannula having a fat-injecting cannula tip;
an ultrasound probe having an ultrasound head; and
a handle having:
   a fixed lower portion from which the fat-injecting cannula extends along a first plane; and
   an adjustable upper portion from which the ultrasound probe extends,
   wherein the adjustable upper portion is connected to and adjustable relative to the fixed lower portion between at least a first position and a second position,
   wherein, in the first position, the ultrasound head is positioned along a second plane that is spaced apart and substantially parallel to the first plane,
   wherein, in the second position, the ultrasound head is positioned along a third plane that forms an acute angle with the first plane, and
   wherein in both the first and second positions, the ultrasound head produces an ultrasound field of view that includes the fat-injecting cannula tip to provide image-guided positioning of the fat-injecting cannula within a patient.

2. The medical device of claim 1, wherein adjustable upper portion of the handle is pivotally connected to fixed lower portion of the handle such that a distance between the ultrasound head and the fat-injecting cannula tip is adjustable by pivoting the adjustable upper portion of the handle relative to the fixed lower portion of the handle.

3. The medical device of claim 2, further comprising a lock usable to hold the adjustable upper portion of the handle in a fixed position relative to the fixed lower portion of the handle.

4. The medical device of claim 3, wherein the lock prevents the ultrasound probe from pivoting.

5. The medical device of claim 3, wherein the lock is spring-loaded.

6. The medical device of claim 2, wherein the adjustable upper portion of the handle comprises a lever adaptable to adjust the distance between the ultrasound head and the fat-injecting cannula tip.

7. The medical device of claim 1, wherein the ultrasound head is a linear head.

8. The medical device of claim 1, further comprising a fat transfer port at a rear portion of the handle, wherein the fat transfer port is in fluid communication with the fat-injecting cannula.

9. The medical device of claim 1, wherein a rear portion of the handle includes a wire connection point for the ultrasound probe.

10. A method of using the medical device of claim 1, comprising:
   adjusting a position of the adjustable upper portion of the handle relative to the fixed lower portion of the handle to the first position;
   inserting the fat-injecting cannula into a fat injection area of a patient;
   contacting a patient's skin with the ultrasound head proximate the fat injection area; and
   injecting fat in the fat injection area while viewing a placement of the fat-injecting cannula tip inside the patient on an ultrasound monitor.

11. The method of claim 10, further comprising single-handedly adjusting the position of the adjustable upper portion of the handle relative to the fixed lower portion of the handle to the second position after adjusting to the first position.

12. The method of claim 11, further comprising locking the adjustable upper portion of the handle in the second position relative to the fixed lower portion of the handle.

13. The method of claim 10, further comprising viewing placement of the fat-injecting cannula tip on the ultrasound monitor in a Doppler mode.

14. A medical device, comprising:
   a fat-injecting cannula having a fat-injecting cannula tip;
   an ultrasound probe having an ultrasound head; and
   a handle having:
      a fixed lower portion from which the fat-injecting cannula extends along a first plane; and
      an adjustable upper portion from which the ultrasound probe extends,
      wherein the adjustable upper portion is pivotally connected to the fixed lower portion and is movable between at least a first position and a second position,
      wherein, in the first position, the ultrasound head is positioned along a second plane that is spaced apart by a first distance from the first plane and is substantially parallel to the first plane,
      wherein, in the second position, the ultrasound head is positioned along a third plane that forms an acute angle relative to the first plane and the ultrasound head is spaced apart from the first plane by a second distance that is greater than the first distance, and
      wherein in both the first and second positions, the ultrasound head produces an ultrasound field of view that includes the fat-injecting cannula tip to provide image-guided positioning of the fat-injecting cannula within a patient.

15. The medical device of claim 14, further comprising a lock usable to hold the adjustable upper portion of the handle and the ultrasound probe extending from the adjustable portion in a fixed position relative to the fixed lower portion of the handle and the cannula tip extending from the fixed lower portion.

16. The medical device of claim 15, wherein the lock prevents the adjustable upper portion of the handle and the ultrasound probe extending from the adjustable portion from pivoting.

17. The medical device of claim 14, wherein the ultrasound head is a linear head.

18. A medical device comprising:
   a fat-injecting cannula having a fat-injecting cannula tip;
   an ultrasound probe having an ultrasound head; and
   a handle having:
      a fixed lower portion from which the fat-injecting cannula extends along a first plane; and
      an adjustable upper portion from which the ultrasound probe extends,
      wherein the adjustable upper portion is connected to and adjustable relative to the fixed lower portion between at least a first position and a second position,
      wherein, in the first position, the ultrasound head is positioned both immediately above the fat-injecting cannula tip and along a second plane that is spaced apart and substantially parallel to the first plane,
      wherein, in the second position, the ultrasound head is positioned along a third plane that forms an acute angle with the first plane, and
      wherein, in both the first and second positions, the ultrasound head produces an ultrasound field of view that includes the fat-injecting cannula tip,
      wherein the fixed lower portion of the handle includes both a fat transfer port that is in fluid communication with the fat-injecting cannula and a wire connection in electrical communication with the ultrasound probe.

* * * * *